US009333049B2

(12) United States Patent
McDonald et al.

(10) Patent No.: US 9,333,049 B2
(45) Date of Patent: May 10, 2016

(54) DOUBLE ENDED TWEEZERS

(71) Applicant: DENTSPLY INTERNATIONAL INC., York, PA (US)

(72) Inventors: Simon P. McDonald, Katikati (NZ); Matthew Backler, Katikati (NZ)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/425,300

(22) PCT Filed: Sep. 20, 2013

(86) PCT No.: PCT/US2013/060923
§ 371 (c)(1),
(2) Date: Mar. 2, 2015

(87) PCT Pub. No.: WO2014/047440
PCT Pub. Date: Mar. 27, 2014

(65) Prior Publication Data
US 2015/0230884 A1    Aug. 20, 2015

(30) Foreign Application Priority Data
Sep. 21, 2012   (NZ) .......................................... 602561

(51) Int. Cl.
*A61C 3/10*        (2006.01)
(52) U.S. Cl.
CPC ...................................... *A61C 3/10* (2013.01)
(58) Field of Classification Search
CPC .. A61C 3/10; A61B 17/30; A61B 2018/1462; A61B 2017/305; A45D 26/00; A45D 26/0066; G04D 1/021; G04D 1/026; G04D 1/00; G04D 1/02

USPC .......... 433/157–162, 3–6; 294/99.2; 606/210, 606/211, 51–52; 968/666
See application file for complete search history.

(56) References Cited

U.S. PATENT DOCUMENTS

| 450,266 A | | 4/1891 | Truax | |
|---|---|---|---|---|
| 1,842,403 A | * | 1/1932 | Hunsaker | ........... A45D 26/0066 294/99.2 |

(Continued)

FOREIGN PATENT DOCUMENTS

| CA | 2038327 A1 | 9/1992 |
|---|---|---|
| CN | 2065897 U | 11/1990 |

(Continued)

OTHER PUBLICATIONS

T. Terasawa; Office Action for Japanese Patent Applicant No. 2015-533221; Aug. 14, 2015, Japan.

(Continued)

*Primary Examiner* — Yogesh Patel
(74) *Attorney, Agent, or Firm* — IpHorgan Ltd.

(57) ABSTRACT

The present invention provides a tweezer for dental and other applications. The tweezer including a main body portion (12, 14) extending in a generally longitudinal direction. The main body portion having a first end (20) and a second end (18). A hinge connector (16) is located between the first end and the second end. A first pair of pincers is located at the first end (20). A second pair of pincers is located at the second end (18). A bias mechanism (22) urges the first pair of pincers (20) into a closed position and urging the second pair of pincers (18) in an open position, whereby the user may apply a force to the tweezers to overcome the bias mechanism (22) and urge the first pair of pincers (20) away from the closed position and the second pair of pincers (18) away from the open position.

20 Claims, 5 Drawing Sheets

(56) References Cited

U.S. PATENT DOCUMENTS

| | | | | |
|---|---|---|---|---|
| 2,711,339 | A * | 6/1955 | McGogy | A47G 21/103 |
| | | | | 294/11 |
| 3,906,957 | A * | 9/1975 | Weston | A61B 17/2804 |
| | | | | 24/562 |
| 4,825,864 | A | 5/1989 | Hariri | |
| 5,060,329 | A | 10/1991 | Hudson | |
| 5,199,756 | A * | 4/1993 | Bartlett | A47J 43/283 |
| | | | | 294/106 |
| 5,385,471 | A | 1/1995 | Chuen | |
| 5,868,787 | A | 2/1999 | Kim | |
| 6,142,781 | A | 11/2000 | Fischer | |
| 6,322,363 | B1 | 11/2001 | Beecher | |
| 6,345,983 | B1 * | 2/2002 | Godfrey | A61C 5/125 |
| | | | | 433/159 |
| 6,776,615 | B2 | 8/2004 | Dietrich | |
| D532,553 | S | 11/2006 | Ross | |
| D559,457 | S | 1/2008 | Garland | |
| D575,904 | S | 8/2008 | Iqbal | |
| 7,625,028 | B2 * | 12/2009 | Cho | B25B 9/02 |
| | | | | 294/99.2 |
| 7,938,469 | B2 | 5/2011 | Ait-Mani | |
| 2002/0094507 | A1 | 7/2002 | Feuer | |
| 2008/0157550 | A1 | 7/2008 | Burgess | |
| 2011/0003265 | A1 | 1/2011 | McDonald | |

FOREIGN PATENT DOCUMENTS

| | | |
|---|---|---|
| CN | 2138969 Y | 7/1993 |
| CN | 201684036 U | 12/2010 |
| DE | 202006007904 U1 | 8/2006 |
| EP | 1199003 A1 | 9/2001 |
| FR | 2553281 A | 4/1985 |
| GB | 2257365 A | 1/1993 |
| JP | S5167782 U | 5/1976 |
| JP | S5731885 A | 2/1982 |
| JP | S6031701 Y | 9/1985 |
| JP | S6353516 U | 4/1988 |
| JP | H4126515 U | 11/1992 |
| JP | 3020361 U | 1/1996 |
| LT | 5798 B | 12/2011 |

OTHER PUBLICATIONS

European Patent Office, International Search Report, PCT/US2013/060923, Nov. 26, 2013.

European Patent Office, International Preliminary Report on Patentability, PCT/US2013/060923, Apr. 2, 2015.

T. Terasawa; Decision of Refusal for Japanese Patent Applicant No. 2015-533221; Dec. 3, 2015, Japan.

* cited by examiner

DOUBLE ENDED TWEEZERS

CROSS-REFERENCE TO RELATED APPLICATIONS

This application is a national phase application of international application no. PCT/US2013/060923, filed Sep. 20, 2013, which claims priority to New Zealand Application No. 602561, filed Sep. 21, 2012, the entire contents of which both are hereby incorporated by reference.

FIELD OF THE INVENTION

The present invention relates generally to the field of dental instruments and more specifically to dental tweezers. The invention may also find application in other fields where tweezers are utilized.

BACKGROUND OF THE INVENTION

Tweezers are instruments used to pick up objects that are too small to be easily handled using human hands. A majority of dental products are small and require the use of tweezers. Dental tweezers come in a variety of sizes and shapes. Dentists usually use more than one type of tweezer during a single procedure. Most tweezers require the application of constant pressure while gripping an object. This requirement is a difficulty when the dental assistant needs to pass the dental product to the dentist. This requirement also doesn't allow for preloading of the tweezers.

Although there are several dental tweezers in prior art (U.S. Pat. No. 6,776,615 B2, U.S. Pat. No. 7,938,469 B2, U.S. Pat. No. 6,142,781 and U.S. Pat. No. 5,060,329), these tweezers don't have tweezers at both ends and also they don't allow for preloading. The current invention aims to address drawbacks in prior art.

SUMMARY OF THE INVENTION

The object of this invention is to provide an instrument that can be used for different purposes and which allows for preloading. The device is a double-ended tweezer wherein both ends include a pair of pincers, and one end is biased in a closed position and the other end is biased in an open position.

The present invention provides a tweezer for dental and other applications, the tweezer comprising a main body portion extending in a generally longitudinal direction. The main body portion having a first end and a second end. A hinge connector is located between the first end and the second end. A first pair of pincers is located at the first end and a second pair of pincers located at the second end. A bias mechanism urging the first pair of pincers into a closed position and urging the second pair of pincers in an open position, whereby the user may apply a force to the tweezers to overcome the bias mechanism and urge the first pair of pincers away from the closed position and the second pair of pincers away from the open position.

DETAILED DESCRIPTION OF THE INVENTION

Figure 1:
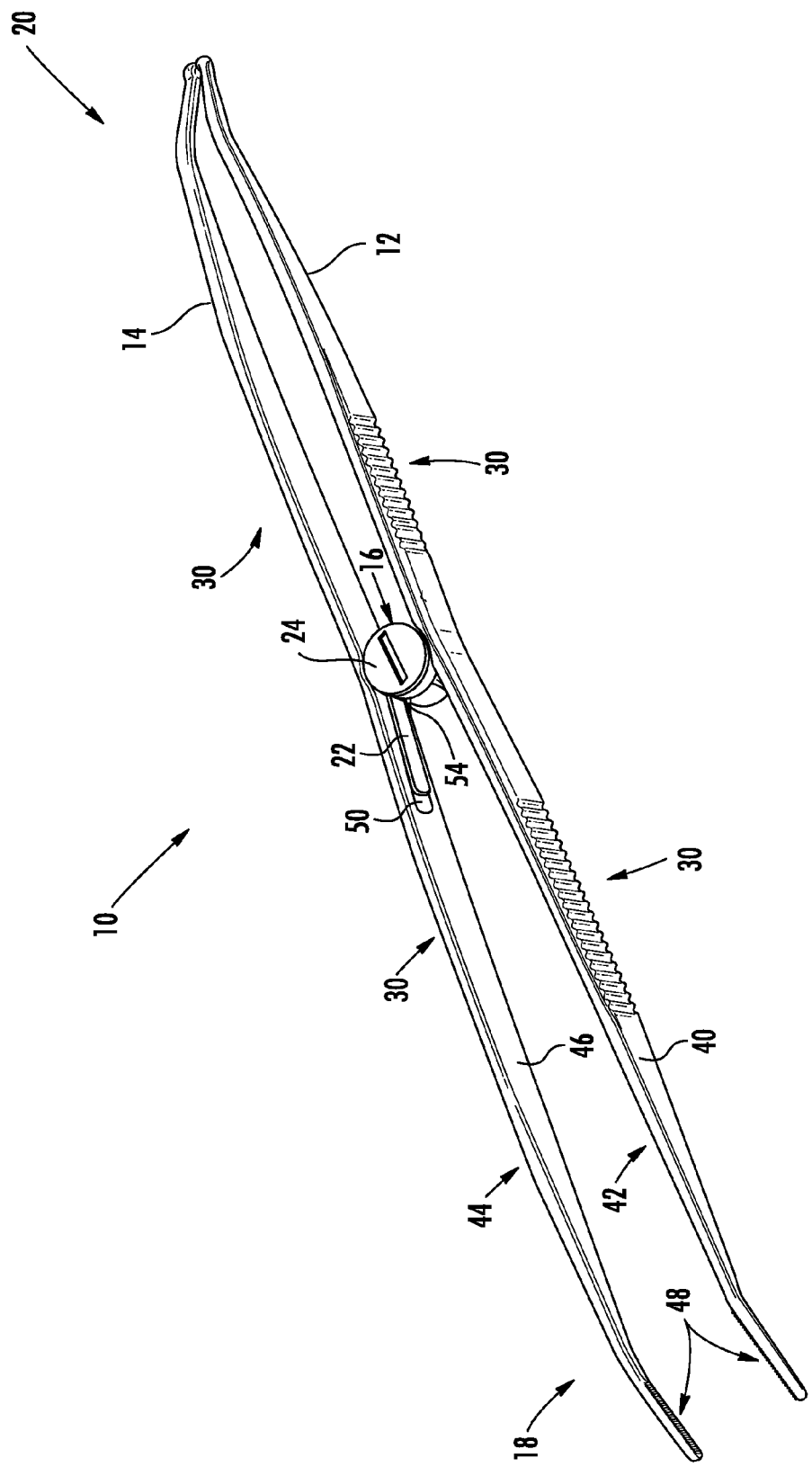
FIG. 1 is a perspective view of a double-ended tweezer in accordance with one embodiment of the present invention, in a passive configuration.

FIG. 1 shows a perspective view of a double-ended tweezer 10 for dental procedures in accordance with one embodiment of the present invention. The double-ended tweezer 10 includes a first lever 12 and a second lever 14. The first lever 12 is coupled to the second lever 14 via a fulcrum or hinge connector 16. The double-ended tweezer 10 includes a pair of pincers at both ends 18, 20. In particular, the double-ended tweezer 10 includes a cotton tweezer end 18 and a pin tweezer end 20.

The hinge connector 16 couples the first lever 12 and second lever 14 in a pivotal manner. The hinge connector 16 includes a spring 22 which biases the tweezer 10 in a passive position as shown in FIG. 1. In the passive position of FIG. 1, the pin tweezer end 20 is urged toward a closed arrangement and the cotton tweezer end 18 is urged towards an open arrangement. The hinge connector 16 also includes a fastener 24 for maintaining the first lever 12 and second lever 14 in a biased pivotal connection.

FIG. 1 also shows that the first lever 12 includes gripping portions 30. Although not readily seen, it will be appreciated that second lever 14 also includes gripping portions 30. The gripping portions may be a series of grooves machined or otherwise provided in the levers. Alternatively, the gripping portions 30 may be provided on one side of a one-sided adhesive label. The other side of the label having the adhesive for applying and retaining the gripping portion 30 to the respective lever. The gripping portions 30 may take the form of other embodiments as will be appreciated.

Figure 2:
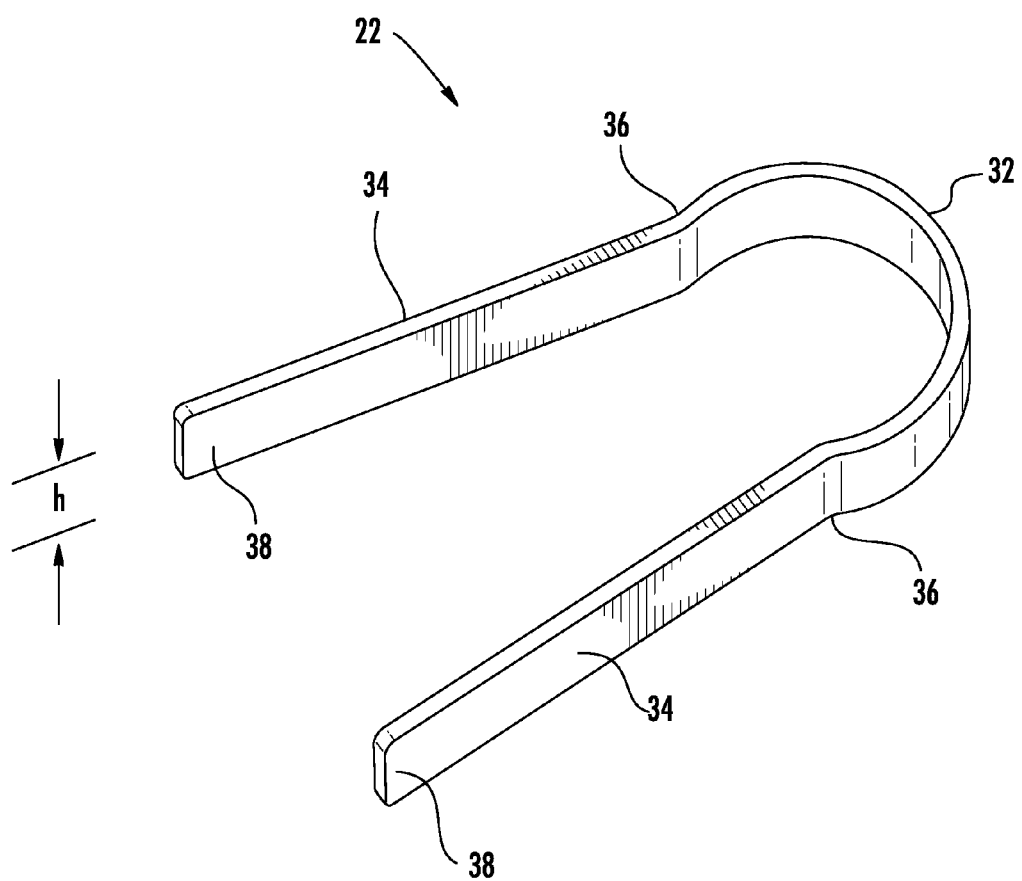
FIG. 2 is a perspective view of a spring of the double-ended tweezer of FIG. 1.

The spring 22 is shown in FIG. 2 to be a keyhole shaped flat metal spring. The spring 22 includes a curved portion 32 with legs 34 extending from the curved portion 32. The spring 22 provides a height "h". The spring 22 includes a transition portion 36 between the curved portion 32 and the respective leg 34. The legs 34 each terminate at ends 38.

The first lever 12 includes an outer wall 40 and an inner wall 42. Similarly, the second lever 14 includes an outer wall 44 and inner wall 46. The cotton tweezer end 18 is shown to include a gripping portion 48 on the opposed facing inner walls 42, 46. The gripping portion 48 may be parallel ribbing, slightly offset so as to provide an overlapping engagement. The inner wall 48 includes a rectangular recess 50 for receiving and retaining a respective end 38 of the spring 22. The inner wall 42 includes a similar recess 50 (not shown) in opposed facing relation with the recess 50 of the inner wall 46.

FIG. 1 shows that the portion of the levers 12, 14 extending from the hinge connector 16 to the cotton tweezer end 18 is longer than the portion of the levers 12, 14 extending from the hinge connector 16 to the pin tweezer end 20. This arrangement accommodates the longer length desired for the cotton tweezers end 18, yet avoids an unduly long overall length of the tweezers 10.

Figure 3:
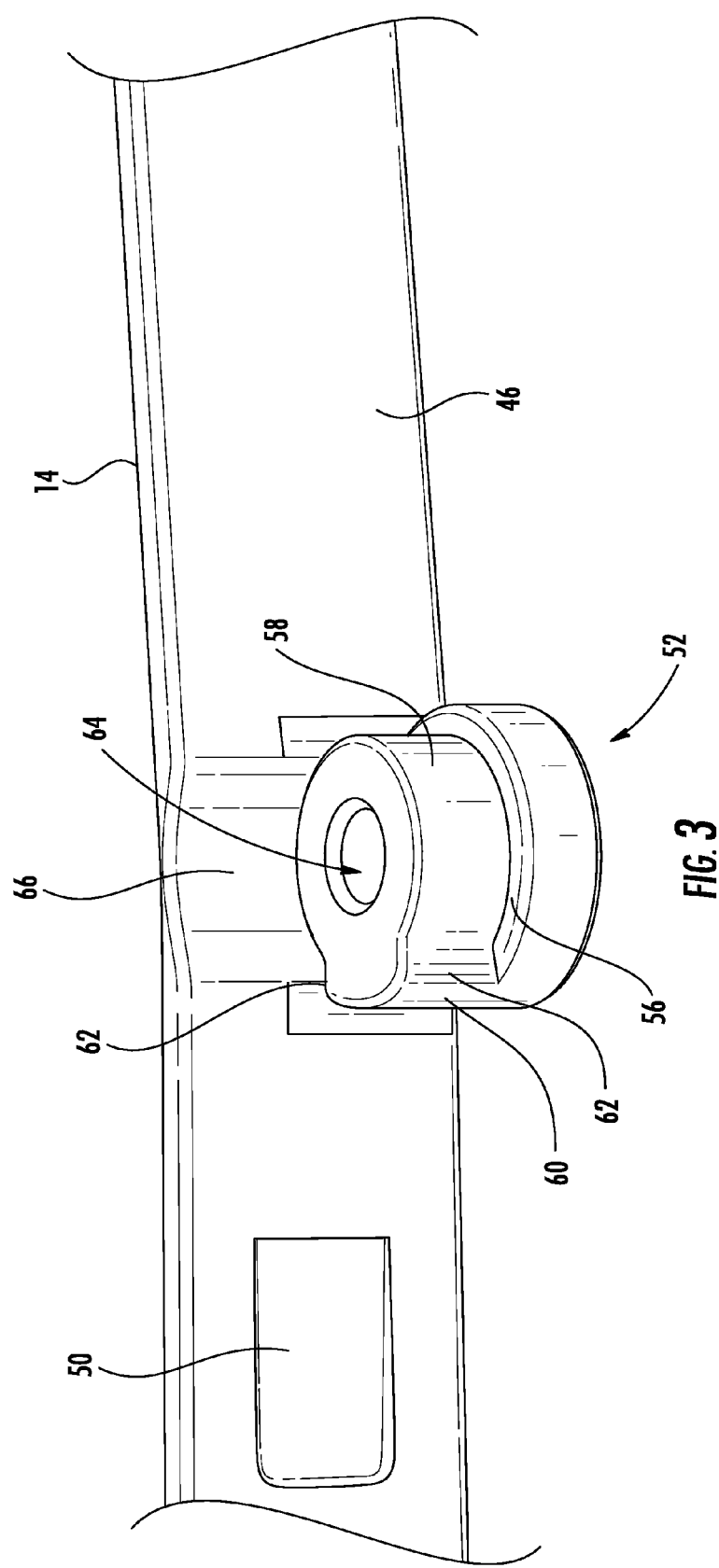
FIG. 3 is a close-up detail of the hinge connector portion of the second lever of the double-ended tweezer of FIG. 1.

FIG. 3 shows a close up exploded view of the second lever 14. In particular, a pivot seat 52 is shown. The pivot seat 52 extends from the inner wall 46 of the second lever 14 via a flange portion 54 (see FIG. 1). The pivot seat 52 includes a C-shaped annular spring abutement 56. A cylindrical spring wall 58 extends from the annular spring abutement 56 and defines a height of the wall 58. The cylindrical spring wall 58 is interrupted by nub 60 which forms a pair a spring leg abutements 62. The nub 60 has a width as defined by the spring leg abutement 62. A hole 64 extends through the pivot seat 52, including the annular spring abutement 56 and cylindrical spring wall 58. FIG. 3 also shows the rectangular recess 50 for receiving and retaining an end 38 of the spring 22. The depth of the rectangular recess 50 is shown to increase as the rectangular recess 50 extends away from the pivot seat 52. FIG. 3 also shows that the inner wall 46 includes a curved recessed portion 66 opposite the pivot seat 52. The recessed portion 66 accommodates the curved portion 32 of the spring 22.

The first lever 12 includes a similar pivot seat 52 and accordingly the same reference numerals are used. However, alternatively, the corresponding wall 58 may provide a height the same or different from the height of the wall 58 of the second lever 14. Regardless, the combined height of both walls 58 may be slightly greater than the height "h" so as not to bind the spring 22. Further, the width of the nub 60 may be narrower than that of the second lever 14. In this manner, the nub 60 of the first lever 12 will not interfere with the spring 22 during pivoting action of the tweezer 10. In addition, the hole 64 may be formed of a different dimension from the hole of the second lever 14. The variation in dimension is intended to accommodate particular fastener 24 as will be appreciated from the following comments.

Figure 4:
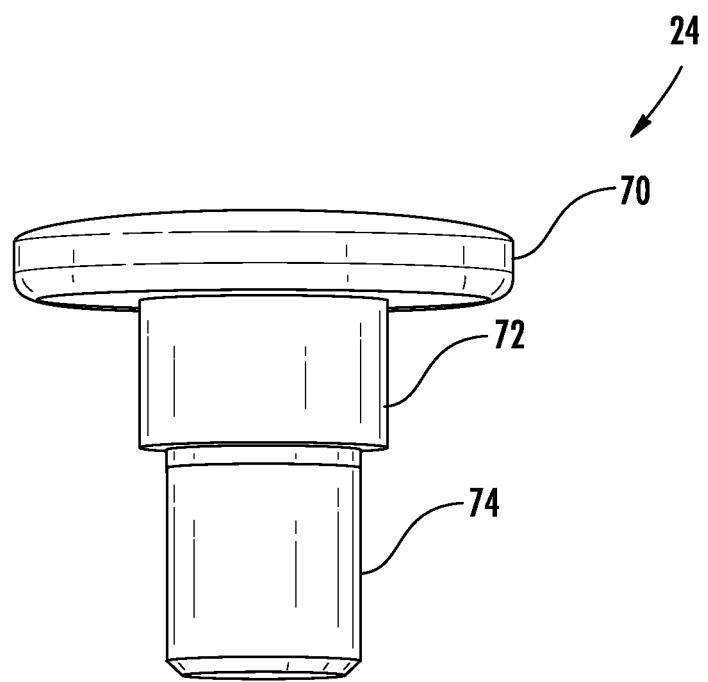
FIG. 4 is a plan view of the fastener of the double-ended tweezer of FIG. 1.

FIG. 4 shows the fastener 24. The fastener 24 includes a slotted head 70, a pivot shank 72 and an end shank 74. The pivot shank 72 includes a diameter which is slightly less than the diameter of the hole 64 in the pivot seat of the first lever 12. The end shank 74 includes a diameter which provides an interference fit with the hole 64 in the pivot seat 52 of the second lever 14. Alternatively, the hole 64 in the pivot seat 52 of the second lever 14 may be threaded, with the end shank 74 having a mating threaded arrangement. Other fastener arrangements are contemplated as will be understood.

Figure 5:
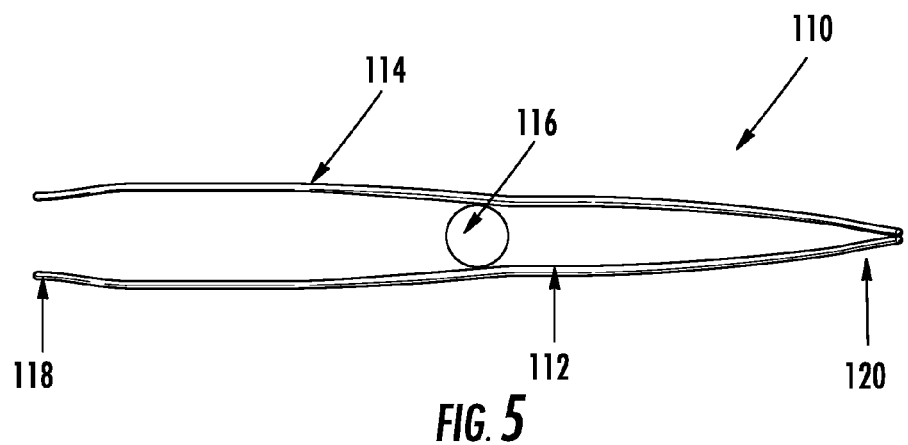
FIG. 5 is a top plan view of a double-ended tweezer in accordance with another embodiment of the present invention, in a passive configuration.
Figure 6:
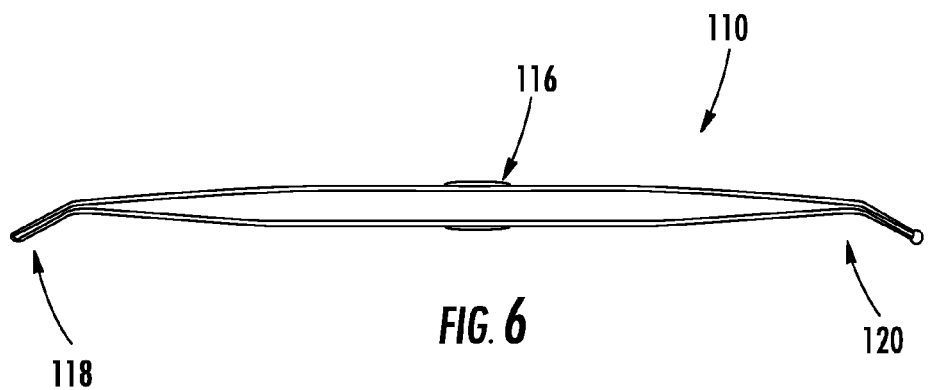
FIG. 6 is a side plan view of the double-ended tweezer of FIG. 5.
Figure 7:
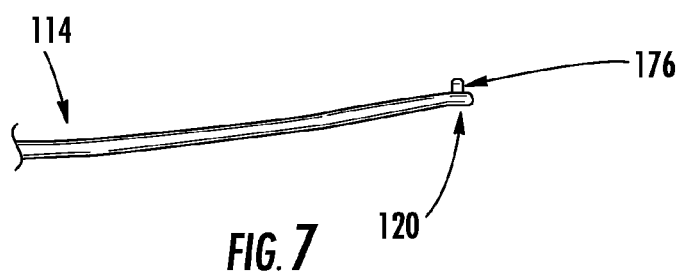
FIG. 7 is a close-up detail of the cotton tweezer end of the second lever of the double-ended tweezer of FIG. 5, showing the pin.
Figure 8:
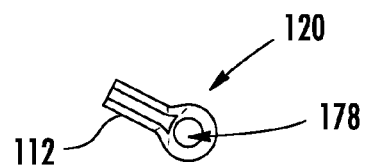
FIG. 8 is a close-up detail of the cotton tweezer end of the first lever of the double-ended tweezer of FIG. 5, showing the pin hole.

FIG. 5 shows a top plan view of a double-ended dental tweezer 110 in accordance with another embodiment of the present invention, in a passive configuration. Where features are similar to the first embodiment, similar reference numerals are used. In this embodiment, the hinge connection 116 is located at a mid-portion of the double-ended dental tweezer 110. FIG. 6 is a side plan view of the double-ended dental tweezer of FIG. 5. FIG. 7 is a close-up detail of the pin tweezer end 120 of the second lever 114 of the double-ended dental tweezer 110 of FIG. 5, showing the pin 176. FIG. 8 is a close-up detail of the pin tweezer end 120 of the first lever 112 of the double-ended dental tweezer 110 of FIG. 5, showing the pin hole 178 for receiving the pin 176.

In the two embodiments shown above, at one end is a combination pin and hole arrangement and at the other end cotton tweezers ends. In yet another embodiment, the ends are the same, e.g., cotton tweezers ends. Other embodiments are also possible and contemplated. The double-ended tweezer may be made of metal. However, other materials are possible and keeping within the spirit of the invention.

The pin-end allows for better gripping of objects that have a hole through them. The pin-end also allows for preloading of the tweezers. A spring keeps the pin-end arms closed. The spring may be inbuilt or separate to the hinge connector.

The device works such that the dentist can handle small dental accessories using one set of tweezers. In the passive configuration, the distal side of the device is open and the proximal side is closed by a spring. The dentist has to apply pressure on the two levers to grip objects at the distal ends. At the proximal end, pressure is applied to open the ends. Once the object has been gripped, the device can be used without the application of pressure. This allows for preloading of the device and for secure handling of the object and device at the chair-side.

The distal side of the device is used for general purposes and the proximal side is used for dental products that allow the use of the pin-ends.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

We claim:

1. A tweezer for dental and other applications, the tweezer comprising:
   a main body portion (12, 14) extending in a generally longitudinal direction, the main body portion having a first end portion (20) and a second end portion (18);
   a hinge connector (16) located between the first end portion (20) and the second end portion (18);
   a first pair of pincers located at the first end portion (20);
   a second pair of pincers located at the second end portion (18); and
   a bias mechanism (22) urging the first pair of pincers (20) into a closed position and urging the second pair of pincers (18) in an open position, whereby a user may apply a force to the tweezer to overcome the bias mechanism and urge the first pair of pincers (20) away from the closed position and the second pair of pincers (18) away from the open position.

2. The tweezer of claim 1, wherein the first pair of pincers (20) and the second pair of pincers (18) are selected from the group comprising a cotton tweezer end (18) and a pin tweezer end (20).

3. The tweezer of claim 1, wherein the first pair of pincers (20) is a pin tweezer end (18) and the second pair of pincers (18) is a cotton tweezer end (18), wherein the pin tweezer end (18) is biased in a closed position.

4. The tweezer of claim 1, wherein the first end portion (20) and the second end portion (18) extend at an angle with respect to the longitudinal direction of the main body portion (12, 14).

5. The tweezer of claim 1, wherein the hinge connector (16) is located at a mid-portion between the first end portion (20) and the second end portion (18).

6. The tweezer of claim 1, wherein the hinge connector (16) is located at position offset from a mid-portion between the first end portion (20) and the second end portion (18).

7. The tweezer of claim 1, wherein the main body portion includes a first lever (12) and a second lever (14), the first lever and second lever having opposed facing inner walls (42, 46), and having outer walls (40, 44).

8. The tweezer of claim 7, wherein the hinge connector (16) includes a lower hinge connector portion (52) extending from the inner wall (46) of the second lever (14), and an upper hinge connector portion (52) extending from the inner wall (42) of the first lever (12) and overlapping the lower hinge connector portion (52), the hinge connector portions (52, 52) each having an opening (64) defining a central axis, wherein both central axes are aligned, and a fastener (24) is received within the aligned openings (64) to provide a pivot hinge connection between the first lever (12) and the second lever (14).

9. The tweezer of claim 8, wherein the fastener (24) includes a pivot shank portion (72) and an end shank portion (74), the pivot shank portion and the end shank portion extend through the aligned openings (64), the openings having respective diameters, the pivot shank portion having a diameter slightly smaller than the diameter of the respective opening of the hinge connector portion, and the end shank portion having a diameter slightly larger than the diameter of the respective opening of the hinge connector portion so as to provide an interference fit.

10. The tweezer of claim 8, wherein the fastener includes a pivot shank portion and an end shank portion, the pivot shank portion and the end shank portion extend through the aligned openings, the openings having respective diameters, the pivot shank portion having a diameter slightly smaller than the diameter of the respective opening of the hinge connector portion, and the end shank portion having a threaded portion, and the respective opening of the hinge connector portion includes a threaded portion for mating engagement with the end shank portion.

11. The tweezer of claim 8, further comprising:
the lower hinge connector portion (52) having a first inner surface, a first outer surface, and a first annular spring abutment (56), wherein the first inner surface is substantially perpendicular to the central axis of the lower hinge connector opening (64) and the first annular spring abutment (56) is located between the first inner surface and the first outer surface;
the upper hinge connector (52) having a second inner surface, a second outer surface, and a second annular spring abutment (56), wherein the second inner surface is substantially perpendicular to the central axis of the lower hinge connector opening (64) and the second annular spring abutment (56) is located between the second inner surface and the second outer surface;
a first arcuate shaped wall (58) extending between the first inner surface and the first annular spring abutment;
a second arcuate shaped wall (58) extending between the second inner surface and the second annular spring abutment;
the first arcuate shaped wall and the second arcuate shaped wall being aligned with each other; and
the bias mechanism (22) having a spring of flat metal shaped to have a curved portion (32) and two legs (34, 34);
wherein the curved portion is arranged around the aligned first arcuate shaped wall (58) and the second arcuate shaped wall (58), and the legs of the spring engage the respective inner wall (42, 46).

12. The tweezer of claim 11, wherein each inner wall includes a recessed area (50) for receiving a portion (38) of the respective leg (34) of the spring (22).

13. The tweezer of claim 8, wherein the lower hinge connector portion (52) includes a pair of spring leg abutments (62) defining a first width, and the upper hinge connector portion (52) includes a pair of spring leg abutments (62) defining a second width.

14. The tweezer of claim 7, wherein the bias mechanism is a spring (22) having a first leg (34) and a second leg (34), each leg in spring biased contact with the respective inner wall (42, 46) at a location spaced apart from the hinge connector (16).

15. The tweezer of claim 7, wherein the main body portion includes gripping portions (30) on the outer walls (40, 44) of the first lever and second lever.

16. The tweezer of claim 1, wherein the bias mechanism (22) is arranged about the hinge connector.

17. The tweezer of claim 1, wherein the bias mechanism (22) is arranged separate from the hinge connector.

18. The tweezer of claim 1, wherein the main body portion (12, 14) and hinge connector (16) are made of metal.

19. The tweezer of claim 1, wherein the main body portion (12, 14) and hinge connector (16) are made of plastic.

20. A tweezer for dental and other applications, the tweezer comprising:
a main body portion (12, 14) extending in a generally longitudinal direction, the main body portion having a first end portion (20), second end portion (18), a first lever (12) and a second lever (14), the first lever and second lever having opposed facing inner walls (42, 46);
a hinge connector (16) located between the first end portion (20) and the second end portion (18), the hinge connector (16) having a lower hinge connector portion (52) extending from the inner wall (46) of the second lever (14), and an upper hinge connector portion (52) extending from the inner wall (42) of the first lever (12) and overlapping the lower hinge connector portion (52), the upper and lower hinge connector portions (52, 52) each having an opening (64) defining a central axis, wherein both central axes are aligned, and a fastener (24) is received within the aligned openings (64) to provide a pivot hinge connection between the first lever (12) and the second lever (14);
the lower hinge connector portion (52) having a first inner surface that is substantially perpendicular to the central axis of the lower hinge connector portion opening (64), a first outer surface, a first annular spring abutment (56) located between the first inner surface and first outer surface, and a first arcuate shaped wall (58) extending between the first inner surface and the first annular spring abutment (56);
the upper hinge connector portion (52) having a second inner surface that is substantially perpendicular to the central axis of the upper hinge connector portion opening (64), a second outer surface, and a second annular spring abutment (56) located between the second inner surface and the second outer surface, and a second arcuate shaped wall (58) extending between the second inner surface and the second annular spring abutment (56), the first arcuate shaped wall (58) and the second arcuate shaped (58) wall being aligned with each other;
a first pair of pincers located at the first end portion (20) and a second pair of pincers located at the second end portion (18); and
a bias mechanism (22) urging the first pair of pincers (20) into a closed position and urging the second pair of pincers (18) in an open position, the bias mechanism (22) having a spring of metal shaped to have a curved portion (32) and two legs (34, 34); wherein the curved portion of the bias mechanism is arranged around the aligned first arcuate shaped wall (58) and the second arcuate shaped wall (58), and the legs of the spring engage the respective inner wall (42, 46);

whereby a user may apply a force to the tweezer to overcome the bias mechanism and urge the first pair of pincers (20) away from the closed position and the second pair of pincers (18) away from the open position.

\* \* \* \* \*